(12) United States Patent
Fusca et al.

(10) Patent No.: US 6,254,886 B1
(45) Date of Patent: Jul. 3, 2001

(54) MULTILAYER TABLET

(75) Inventors: Martino Fusca, Nackenheim; Dagmar Färber, Heppenheim, both of (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/151,733

(22) Filed: Sep. 11, 1998

(30) Foreign Application Priority Data

Dec. 19, 1997 (EP) ................................................. 97122492

(51) Int. Cl.[7] ............................... A61K 9/20; A61K 9/24; C12N 1/20; C12N 1/16
(52) U.S. Cl. ........................ 424/464; 424/472; 435/252.1; 435/252.9; 435/255.2
(58) Field of Search ................................... 424/464, 472; 435/252.1, 252.9, 255.2

(56) References Cited

U.S. PATENT DOCUMENTS

| | | | |
|---|---|---|---|
| 4,806,368 | * | 2/1989 | Reddy ..................................... 426/61 |
| 4,888,171 | * | 12/1989 | Okonogi et al. ........................ 424/93 |
| 5,275,943 | * | 1/1994 | DiTuro .................................. 435/179 |
| 5,531,989 | * | 7/1996 | Paul ..................................... 424/93.4 |
| 5,705,152 | * | 1/1998 | Plummer ............................. 424/93.45 |

OTHER PUBLICATIONS

Abstract of JP 05186337, Masaaki, Jul. 27, 1993.
Abstract of JP 08143463, Katsuji, Jun. 4, 1996.

* cited by examiner

*Primary Examiner*—Diana Dudash
*Assistant Examiner*—Alysia Berman
(74) *Attorney, Agent, or Firm*—Millen White Zelano & Branigan

(57) ABSTRACT

The invention relates to multilayer tablets which are constructed of two, three or more layers, one layer containing probiotic microorganisms, while the other layers contain foodstuff ingredients valuable in nutritional physiology, such as vitamins, minerals, etc. The tablets are distinguished by a high stability or activity over a long period with respect to the microorganisms used and are thus very well suited for keeping in storage.

17 Claims, No Drawings

MULTILAYER TABLET

The invention relates to multilayer tablets which are constructed of two, three or more layers, one layer containing probiotic micro-organisms, while the other layers contain foodstuff ingredients valuable in nutritional physiology, such as vitamins, minerals, etc. The tablets are distinguished by a high stability and/or efficacy over a long period with respect to the micro-organisms used and are thus very well suited for keeping in storage.

Many people, in particular in the economically and industrially highly developed countries, often complain about temporary or chronic digestive symptoms, caused by a damaged or disordered intestinal flora. The causes of these "affluent society disorders" are usually stress situations, medicaments or drug abuse, sequelae of antibiotic treatments or alternatively very often false nutrition. Acute and drastic symptoms can be treated using known pharmaceuticals which can comprise not only suitable pharmaceutical active ingredients but also appropriate natural enzymes or intestine-specific micro-organisms.

In the case of constant, slight disorders of the intestinal tract not directly to be described as illness, however, even the regular consumption of suitable, specially chosen foodstuffs or nutritional supplement preparations based on micro-organisms is often sufficient to alleviate or to eliminate the symptoms which cause a disordered or damaged intestinal flora. However, even in the case of intact or healthy intestinal flora, the supply of probiotic micro-organisms, in particular in connection with antioxidants, can lead to immunostimulating action.

Yoghurt and sour milk products for these reasons are also enjoying increasing popularity. Most of these products valuable for nutrition, which contain suitable micro-organism cultures for the purpose mentioned, are, however, fresh goods and can thus only be stored with cooling and even then only for a few days.

Products which offer the appropriate micro-organisms as a monopreparation are not permissible as a foodstuff or foodstuff supplement in many countries, because they do not contain any substances valuable in nutritional physiology, such as minerals, fats, vitamins, carbohydrates, proteins, bulk materials or trace elements, such as are present precisely in adequate amounts in foodstuffs.

Moreover, it was found that dry preparations based on probiotic micro-organisms positively stimulating the intestinal flora, in particular if they contain foodstuff additives of the abovementioned type, are extremely unstable with respect to their content of biologically active micro-organisms. Even in products which exclusively contain appropriate cultures without such additives, in some cases after only short periods dramatic losses of live micro-organisms would be found ("Probiotics, the Friendly Bacteria"; Heath Which?, 1997, 134).

It was thus the object to make available preparations in the foodstuffs sector, in particular for the constantly growing market "functional food", which on the one hand contain an adequate amount of foodstuff ingredients valuable in nutritional physiology, such as vitamins, minerals, bulk materials, etc., but on the other hand contain a large number of probiotically active micro-organisms stabilizing the intestinal flora, which remain stable despite these additives.

This object was achieved by the provision of a multilayer tablet for the foodstuffs sector. In this tablet, the probiotic micro-organisms are made available in a separate layer. The other foodstuff additives are present in a further layer or a number of other layers. Surprisingly, the stability of the probiotic micro-organisms in the tablets according to the invention is often even higher than in the known preparations which are not permissible under foodstuffs law, which exclusively contain probiotic cultures.

The invention thus relates to a multilayer tablet for the foodstuffs sector, which within a carrier material contains substances valuable in nutritional physiology, and which is characterized in that it consists of at least two separate layers, in one layer exclusively probiotic micro-organisms being present.

Layer tablets having three layers are particularly advantageous. It has turned out as a matter of fact that even with respect to the stability of the other additives, which can be substances of different type, which are more or less sensitive and have a mutual effect, or interfere, such as, for example, vitamins (e.g. β-carotene, vitamin C, vitamin B complex), proteins, sugar alcohols having a reducing action (e.g. sorbitol, mannitol), oxidation-sensitive enzymes or coenzymes or else alternatively physiologically active plant extracts, good results are obtained with multilayer tablets. By means of the multilayer construction of the tablets according to the invention, it is thus possible not only to markedly increase the stability and storability of the micro-organisms used, but also that of the other substances which are prone to instability on interaction with one another. The invention thus relates to a corresponding three-layer tablet. However, tablets having three or more layers, i.e., for example, three, four or five layers, are also possible.

The prerequisite for good stability with respect to the number of live and active micro-organisms in the tablet according to the invention, apart from the multilayer construction of the tablet (where the micro-organisms are present in a separate layer without any other of the foodstuff additives mentioned), is the necessity that the said layer, in particular the carrier material used, in which the micro-organisms are embedded, has a water content of not more than 0.1%.

This can be brought about by drying the carrier material very carefully before mixing with the micro-organism culture (as a rule at 100–120° C. over a period of at least 60 minutes). The invention thus relates to a corresponding multilayer tablet, which is characterized in that the water content of the probiotic layer is at most 0.1%.

Carrier materials, or a tablet base, used for the individual layers are the substances customary for tablets and coated tablets, which are well known in the prior art, i.e., for example, the following compounds, providing, according to the country in which the tablets are used, they are permissible under foodstuffs law: starch (e.g. maize starch), talc, microcrystalline cellulose, lactose, highly disperse silica, polyvinylpyrrolidone or cellulose powder. Other constituents of the tablet base (e.g. binders and disintegrants) which can also be employed are, for example, carbohydrates, such as mannitol, sorbitol, xylitol, glucose, sucrose, fructose, maltose, dextrose, maltodextrin, kaolin or cellulose derivatives such as methylcellulose, hydroxypropylcellulose or hydroxypropylmethylcellulose, as well as calcium carbonate, calcium, magnesium or glyceryl stearate and also colourants and flavourings. The proportionate composition of these base substances depends on the one hand, of course, on the desired content of actual active substances, such as micro-organisms, vitamins, enzymes, bulk materials etc., and on the other hand on criteria which determine the mechanicophysical properties of the tablet or of its layers, such as, for example, hardness, compressibility, size, shape etc.

In most cases, the proportion of the carriers and auxiliaries mentioned (e.g. lubricants and release agents, aromatic substances, colourants, flavourings, stabilizers, antioxidants) is between 1 and 80% based on the total tablet, which according to the invention has a mass of between 0.5 and 1.5 g, preferably approximately 1 gramme. The proportion of the auxiliaries is 1 to 20%.

The amount of the micro-organisms which are employed in tabletting typically according to the invention is between $10^8$ and $10^{10}$ active micro-organisms per tablet. A lower content of cultures no longer guarantees the desired effect on the intestinal flora. The construction and the manner of production of the tablets according to the invention ensure that losses of live cultures are barely to be observed even during a long period. Thus when using $10^{10}$ cultures in preparation of the tablets, after two years' storage at 20° C. and at most 50% atmospheric humidity there are still more than $10^9$ active micro-organisms detected in the tablets independently of which other substances valuable in nutritional physiology are present in the adjacent layers. Prior commercially available preparations which are not based on a multilayer construction in tablet form in some cases have dramatic losses of live cells (factor 10 to 1000).

The invention thus relates to a multilayer tablet which contains at least $10^8$ probiotic micro-organisms in one layer. The invention relates in particular to a corresponding multilayer tablet, which is characterized in that the probiotic layer contains at least $10^8$ active probiotic micro-organisms over a storage period of at least two years under conditions customary for tablets and without cooling. It is thus ensured that, without special storage conditions (in particular cooling), the tablets can be stored in their packs for a commercially customary intended average storage period of six months to a year or or in the pharmacist's shelves or drawers without loss of activity.

Suitable micro-organisms which can be present in the tablets according to the invention are in principle all so-called probiotic cultures. According to the invention, micro-organisms described as probiotic are all those which are either customarily present in the healthy intestinal flora themselves or exert a positive influence on the healthy, disordered or diseased intestinal tract. Such micro-organisms are adequately known and in most cases appropriate strains of such cultures for the foodstuffs sector are also commercially available. Suitable micro-organisms within the meaning of the invention are especially bacteria and yeasts. Examples of these, without thereby restricting the invention, are: *Bifidobacterium bifidum, Bifidobacterium longum, Lactobacillus casei, Lactobacillus acidophilus, Saccharomyces thermophilus* and *Saccharomyces boulardii*. Of course, mixtures of different types of micro-organisms can also be employed in a layer.

The substances which are available in nutritional physiology and which can be present in the tablets according to the invention in common layers or layers separated from one another but not in the layer containing the probiotic micro-organisms include, according to the invention, in particular vitamins such as vitamin A (β-carotene), vitamin C, vitamin E, vitamins of the B complex or vitamin K. The so-called ACE vitamins are of particular interest here. In this case, the vitamins can be present individually or as a mixture. Sometimes, it is recommended to make available water-soluble and fat-soluble (e.g. β-carotene, vitamin B12) vitamins in separate layers. The amount of vitamin per tablet depends as a rule on the daily minimum required dose of the particular vitamin, which can be exceeded by on average 50–200%. For vitamin C, this is approximately 100 to 300 mg, for vitamin E 10 to 50 mg, for β-carotene up to 15 mg and for vitamin B complex 40 to 70 mg.

The invention thus relates in particular to a multilayer tablet for the foodstuffs sector, which within a carrier material contains substances valuable in nutritional physiology, which is characterized in that it consists of two layers, the first layer exclusively containing at least $10^8$ probiotic micro-organisms and the second layer containing vitamin C or a mixture of the vitamins A (β-carotene) and C or a mixture of the vitamins A (β-carotene), C and E.

The invention also relates to a multilayer tablet for the foodstuffs sector, comprising within a carrier material substances valuable in nutritional physiology, which is characterized in that it consists of three layers, an outer layer exclusively containing at least $10^8$ probiotic micro-organisms, the second layer containing vitamin C or a mixture of the vitamins A (β-carotene) and C or a mixture of the vitamins A (β-carotene), C and E, and the third layer containing at least one vitamin of the vitamin B complex.

Furthermore, natural bulk materials, e.g., proteinaceous materials, can be present within specific layers in the tablets according to the invention. Natural bulk materials which can be mentioned, by way of example, are finely ground soya, maize or wheat bran or alternatively crushed grain. On account of taste and colour criteria, soya bran is preferred. The content of bulk materials varies according to the invention between 2 and 50% per tablet, depending on how many layers the tablet is composed of.

Furthermore, individual layers can also contain mineral salts between 5 and 45% based on the total tablet. Possible mineral salts which exert an influence on the human ion balance are, for example, inorganic or organic sodium, potassium, calcium, magnesium or iron salts suitable for consumption, e.g. carbonates, bicarbonates, phosphates, biphosphates, sulfates, bisulfates, chlorides, fluorides, citrates or lactates. In addition, trace elements such as, for example, selenium can also be present in such layers.

Additionally, it is possible in preferably separate layers for enzymes promoting gastric and intestinal functions, as well as enzymes or coenzymes often sensitive to oxidation and moisture (e.g. coenzyme Q), which are favourable for the metabolism or other functions in the human body, to be introduced in amounts known per se. In addition, probiotic substances, and their synthetic counterparts, such as inulin or oligofructose or other oligosugars, can also be present in the various layers of the tablets according to the invention. Finally, it may also be intended that individual layers contain plant extracts, such as, for example, dry extracts from Echinaceae.

The tablets according to the invention can be produced in two different ways:

The dry or pre-dried powder mixtures of carriers and auxiliaries (e.g., release agents) and active ingredients (micro-organisms, vitamins, proteins, etc.) are carefully layered one over the other in a commercially available tabletting machine in two, three or more layers. It must again be emphasized here that the layer which contains the micro-organisms should contain no further active ingredients (destabilizing these), but only carriers and auxiliaries and, if appropriate, inert active ingredients which do not contribute to the destruction of living cells. These carriers must, according to the invention, be very well predried and have a water content of at most 0.1%. For process engineering reasons, it may be advantageous that the layer which contains the micro-organisms is an outer layer, but this can also be an inner layer in tablets having more than two layers. The powder layers layered one over the other in this way are then finally tabletted to give a multilayer tablet. The press pressure is selected to be between 50 and 120 Newtons.

Alternatively to this tabletting method, the individual layers can be preformed separately per se, press pressures of between 20 and 80 Newtons being the rule. The layers preformed in this way are then pressed at press pressures of between 50 and 120 Newtons to give the finished multilayer tablet. This pressing method has the advantage that the layers which have a different compressibility on account of their different composition can be exposed to individual press pressures, which can be advantageous both with respect to the shelf life of the multilayer tablet as a whole and with respect to the stability of the active ingredients in the individual layers. In addition, the boundary layer between two layers in juxtaposition has a smaller active surface due to the preforming, whereby the possibility of the reaction or destabilization of sensitive active ingredients, including the micro-organisms, in the two layers is reduced.

The following examples illustrate the invention, without at the same time wishing to restrict it.

In the foregoing and in the following examples, all temperatures are set forth uncorrected in degrees Celsius; and, unless otherwise indicated, all parts and percentages are by weight.

EXAMPLES

Example 1

Into a commercially available tablet press is initially introduced a pulverulent first layer consisting of maize starch, probiotic bacteria of Lactobacillus acidophilus and glyceryl stearate and over it a second layer of maize starch and a mixture of the vitamins β-carotene, C and E. The first layer contains between $10^8$ and $10^{10}$ bacteria in 500 mg of maize starch (30 mg of glyceryl stearate). The second layer comprises 100 mg of vitamin C, 40 mg of vitamin E and 10 mg of β-carotene mixed with 250 mg of maize starch (altogether 900 mg). The maize starch used is dried at 105° C. for 90 minutes beforehand and after this has a water content of 0.075%. The layers are compressed in one operation using a press pressure of 80 Newtons to give a two-layer tablet.

Example 2

Analogously to Example 1, a two-layer tablet is produced which comprises 150 mg of vitamin C in the second layer.

Example 3

Analogously to Example 1, a two-layer tablet is produced whose second layer contains 200 mg of finely ground soya bran and 50 mg of mineral salt mixture instead of the vitamins.

Example 4

Into a commercially available tablet press is initially introduced a pulverulent first layer consisting of maize starch, probiotic bacteria of Bifidobacterium bifidum and glyceryl stearate as release agent, over it a second layer of maize starch (+release agent) and a mixture of the vitamins β-carotene, C and E, and a third layer of maize starch (+release agent) and vitamin B complex). The first layer contains between $10^8$ and $10^{10}$ bacteria in 500 g of maize starch. The second layer contains 100 mg of vitamin C, 40 mg of vitamin E and 10 mg of β-carotene mixed with 250 mg of maize starch, and the third layer contains 10 mg of vitamin B complex in 100 mg of maize starch. The maize starch used is dried at 105° C. for 90 minutes beforehand and after this has a water content of 0.075%. The layers are compressed in one operation using a press pressure of 110 Newtons to give a three-layer tablet.

Example 5

Analogously to Example 4, a three-layer tablet is produced which in the third layer contains a mixture of mineral salts (250 mg) instead of the vitamin B complex.

Example 6

Analogously to Example 4, a three-layer tablet is produced, the middle layer containing the probiotic microorganisms.

Example 7

A two-layer tablet is produced analogously to Example 1. However, the two layers are individually preformed (press pressure 40 Newtons). Compression is then carried out to give a single two-layer tablet (press pressure 90 Newtons).

Example 8

A three-layer tablet is produced analogously to Example 4. However, the three layers are individually prepressed (press pressure 40 Newtons). Compression is then carried out to give a single three-layer tablet (press pressure 100 Newtons).

Example 9

A two-layer tablet is produced analogously to Example 1, the second layer containing 400 mg of an Echinaceae dry extract instead of the vitamins.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A multilayer tablet for the foodstuffs sector, comprising three layers, wherein at least one layer consists essentially of between about $10^8$ and $10^{10}$ probiotic microorganisms, and at least one layer consists essentially of a carrier material and substances valuable in nutritional physiology which are vitamins, minerals, carbohydrates, proteins, co-enzymes, plant extracts, trace elements, enzymes and/or fats, said tablet being pharmaceutically acceptable as a foodstuff for humans.

2. The multilayer tablet according to claim 1, wherein the water content of the probiotic layer is at most 0.1%.

3. The multilayer tablet according to claim 1, wherein said microorganisms are active in nutritional physiology over a storage period of at least two years under conditions customary for tablets and without cooling.

4. The multilayer tablet according to claim 1 which contains one or more probiotic microorganisms selected from the group consisting of *Lactobacillus casei, Lactobacillus acidophilus, Bifidobacterium bifidum, Bifidobacterium longum* and *Saccharomyces boulardii*.

5. A multilayer tablet for the foodstuffs sector, comprising three layers, wherein at least one layer consists essentially of between about $10^8$ and $10^{10}$ probiotic microorganisms and a second layer contains vitamin C or a mixture of the vitamins β-carotene and C or a mixture of the vitamins β-carotene, C and E.

6. The multilayer tablet of claim 5, wherein the third layer contains at least one vitamin of the vitamin B complex.

7. A process for the production of a multilayer tablet according to claim 1, comprising dispensing said substances in layers and jointly compressing them, or preforming each of said layers individually and compressing them to provide a single tablet.

8. A multilayer tablet according to claim 1, wherein said carrier material is starch, talc, microcrystalline cellulose, highly disperse silica, polyvinyl pyrrolidone, or cellulose powder.

9. A multilayer tablet according to claim 1, wherein said layer comprising microorganisms as an outer layer.

10. A multilayer tablet according to claim 1, wherein said layer comprising microorganisms is a middle layer.

11. A multilayer tablet according to claim 1 which comprises natural bulk material selected from soya, maize, or wheat bran, which in each case is finely ground or crushed.

12. A multilayer tablet according to claim 1 which comprises mineral salts selected from sodium, potassium, calcium magnesium or iron salt, which in each case is inorganic or organic.

13. A multilayer tablet according to claim 1 which comprises a layer that contains one or more enzymes which promote gastric or intestinal functions.

14. A multilayer tablet according to claim 1 which comprises a layer that contains one or more co-enzymes.

15. A multilayer tablet according to claim 1 which comprises inulin or an oligosugar.

16. A multilayer tablet according to claim 1 which comprises plant extract.

17. A method of enhancing nutrition in a human, comprising administering a multilayer tablet of claim 1.

\* \* \* \* \*